United States Patent [19]

Jung

[11] Patent Number: 4,868,173

[45] Date of Patent: * Sep. 19, 1989

[54] CEPHALOSPORIN DERIVATIVES

[75] Inventor: Frederic H. Jung, Rilly la Montagne, France

[73] Assignee: ICI Pharma, Cergy, France

[*] Notice: The portion of the term of this patent subsequent to Jul. 7, 2004 has been disclaimed.

[21] Appl. No.: 798,804

[22] Filed: Nov. 15, 1985

[30] Foreign Application Priority Data

Nov. 20, 1984 [EP] European Pat. Off. ........ 84402358.0

[51] Int. Cl.$^4$ .................. C07D 501/56; A61K 31/545
[52] U.S. Cl. .................................... 514/202; 514/203; 540/222; 540/224; 540/225
[58] Field of Search .................. 260/249.2 R, 249.2; 514/202, 203; 540/222, 225, 224

[56] References Cited

U.S. PATENT DOCUMENTS

| | | | |
|---|---|---|---|
| 4,252,802 | 2/1981 | Denzel et al. | 424/246 |
| 4,278,793 | 7/1981 | Dürckheimer et al. | 544/27 |
| 4,678,781 | 7/1987 | Jung | 514/200 |

FOREIGN PATENT DOCUMENTS

| | | |
|---|---|---|
| 0018155 | 10/1980 | European Pat. Off. |
| 0018595 | 11/1980 | European Pat. Off. |
| 0088320 | 9/1983 | European Pat. Off. |
| 0088853 | 9/1983 | European Pat. Off. |
| 0099297 | 1/1984 | European Pat. Off. |
| 0127992 | 12/1984 | European Pat. Off. |
| 0164944 | 12/1985 | European Pat. Off. |
| 1155493 | 6/1969 | United Kingdom |
| 1399086 | 6/1975 | United Kingdom |
| 2017702 | 10/1979 | United Kingdom |
| 2036738 | 7/1980 | United Kingdom |
| 2046261 | 11/1980 | United Kingdom |
| 2068958 | 8/1981 | United Kingdom |
| 2071664 | 9/1981 | United Kingdom |
| 1604724 | 12/1981 | United Kingdom |
| 2104888 | 3/1983 | United Kingdom |
| 2105719 | 3/1983 | United Kingdom |
| 2117770A | 10/1983 | United Kingdom |

OTHER PUBLICATIONS

Journal of Medicinal Chemistry, 1974, vol. 17, No. 12, pp. 1312–1315, "Semisynthetic-Lactam Antibiotics. 6$^1$ Sulfocephalosporins and Their Antipseudomonal Activities".

Primary Examiner—Nicholas S. Rizzo
Attorney, Agent, or Firm—Cushman, Darby & Cushman

[57] ABSTRACT

According to the invention there is provided a antibacterial cephalosporin derivative of the formula:

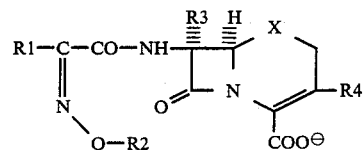

in which X is sulphur, oxygen, methylene or sulphinyl; R3 is hydrogen or methoxy; R1 and R2 are known in the cephalosporin art and R4 is an aminomethyl group in which the amino group carries one of various positively charged nitrogen-containing species set out in the specification and optionally a further substituent selected from hydrogen, lower alkyl, benzyl or heteroarylloweralkyl groups.

9 Claims, No Drawings

CEPHALOSPORIN DERIVATIVES

This invention relates to cephalosporin derivatives which have antibacterial activity.

According to the invention there is provided a cephalosporin derivative of the formula I (formulae given hereinafter) in which X is sulphur, oxygen, methylene or sulphinyl (R or S configuration);

R1 is 2-aminothiazol-4-yl or 2-aminooxazol-4-yl each optionally substituted in the 5-position by fluorine, chlorine or bromine, or R1 is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R2 is hydrogen, (1-6C)alkyl, (3-8C)cycloalkyl, (1-3C)alkyl(3-6C)cycloalkyl, (3-6C)cycloalkyl(1-3C)alkyl, (3-6C)alkenyl, (5-8C)cycloalkenyl, (3-6C)alkynyl, (2-5C)alkylcarbamoyl, phenylcarbamoyl, benzylcarbamoyl, triphenylmethyl, (1-3C)haloalkyl, (2-6C)hydroxyalkyl, (1-4C)alkoxy(2-4C)alkyl, (1-4C)alkylthio(2-4C)alkyl, (1-4C)alkanesulphinyl(1-4C)alkyl, (1-4C)alkanesulphonyl(1-4C)alkyl, (2-6C)aminoalkyl, (1-4C)alkylamino(1-6C)alkyl, (2-8C)dialkylamino(2-6C)alkyl, (1-5C)cyanoalkyl, (1-4C)azidoalkyl, (2-5C)ureidoalkyl, 3-amino-3-carboxypropyl, 2-(amidinothio)ethyl, 2-(N-aminoamidinothio)ethyl, tetrahydropyran-2-yl, thietan-3-yl or 2-oxotetrahydro-furan-3-yl, or —R2 is of the formula —$(CH_2)_v$—R6 in which v is 1 to 4 and R6 is piperidino, pyrrolidino, morpholino, piperazino or N-methylpiperazino, each value of R6 being optionally substituted by (1-4C)alkyl, phenyl or benzyl, or —R2 is of the formula —$(CH_2)_m$—W—R7 in which m is 0 to 3, W is sulphur or a direct bond, and R7 is phenyl or pyridinio(1-4C)alkylene or R7 is pyridyl, imidazolyl, 1,3,4-thiadiazolyl, tetrazolyl, 1-(1-4C)alkyltetrazolyl, thiazolyl, isothiazolyl or isoxazolyl in which the link with X is via a carbon or uncharged nitrogen, each value of R7 being optionally substituted, where possible, by one or two groups selected from (1-4C)alkyl, amino, hydroxy, carboxy, carbamoyl, nitro, (2-5C)alkoxycarbonyl, cyano or sulpho, or —R2 is of the formula —$(Ch_2)_v$—CO—R8 in which v is 1 to 4 and R8 is (1-4C)alkyl, phenyl or benzyl, or —R2 is of the formula —COR9 or —$(Ch_2)_v$—OCO—R9 in which v is 1-4 and R9 is hydrogen, (1-4C)alkyl, (1-4C)haloalkyl, phenyl or benzyl, or —R2 is of the formula —G—$CH_2$—R10 in which G is carbonyl or a direct bond and R10 is phthalimido, or —R2 is of the formula —NR11R12R13 in which R11, R12 and R13 are (1-4C)alkyl, or R11 is (1-4C)alkyl and R12 and R13 are joined to form a (3-6C)carbocyclic ring, or R11, R12 and R13 are joined to form a 1-azonia-4-azabicyclo[2,2,2]octane or 1-azonia-3,5,7-triazatricyclo[3,3,1,1$^{3,7}$]decane, or —R2 is of the formula II in which p is 1 or 2 and R14 and R15 are hydrogen or (1-4C)alkyl, or —R2 is of the formula —P(O)R16R17 in which R16 is hydroxy, (1-4C)alkoxy, (2-8C)dialkylamino, phenoxy, phenylamino or one of the values given above for R6, and R17 is (1-4C)alkyl, (1-4C)alkoxy, (2-8C)dialkylamino, phenoxy, phenylamino, piperidino, pyrrolidino, morpholino, piperazino or N-methylpiperazino, or —R2 is of the formula —$CH_2$P(O)R18R19 in which R18 and R19 are hydroxy or (1-4C)alkoxy, or —R2 is of the formula —CH(SR20)COOR21 in which R20 is (1-4C)alkyl and R21 is hydrogen or (1-6C)alkyl, or —R2 is of the formula III in which m is 0-3, R22 is hydrogen, (1-3C)alkyl or methylthio, R23 is hydrogen, (1-3C)alkyl, ($C_3$—$C_7$)-cycloalkyl, cyano, carboxy, (2-5C)carboxyalkyl or methanesulphonylamino, or phenyl optionally substituted by amino or hydroxy, or R22 and R23 are joined to form, together with the carbon to which they are attached, a (3-7C) carbocyclic ring, adn R24 is hydroxy, amino, (1-4C)alkoxy, (1-4C)alkylamino, phenylamino or of the formula R6 given above or of the formula NHOR25 in which R25 is hydrogen, (1-4C)alkyl, phenyl or benzyl, provided that when R2 contains phenyl, and unless otherwise stated, the phenyl is optionally substituted by 1 or 2 groups selected from halogen, hydroxy, amino, carboxy, nitro, carbamoyl, cyano and aminomethyl;

R3 is hydrogen, or methoxy;

—R4 is of the formula IV,V,VI, or VII: in which n is 1-3;

R26 is hydrogen, (1-4C)alkyl, benzyl or $CH_2$-heteroaryl in which the heteroaryl ring is a 5- or 6-membered aromatic ring containing 1,2 or 3 hetero atoms selected from 0, N and S;

R27 and R28 are selected from hydrogen, halogen, (1-4C)alkyl and phenyl;

R29 is hydrogen, (1-4C)alkyl or phenyl;

R30 is hydrogen, (1-4C)alkyl, phenyl or benzyl;

R31 is hydrogen, amino, (1-4C)alkyl, (3-6C)cycloalkyl, (3-6C)alkenyl, (2-8C)alkoxyalkyl, —$(Ch_2)_t$—COOR38, —$(Ch_2)_t$—CONH_2, —$(Ch_2)_t$—NHCO—R39 or —$(Ch_2)_t$S(O)$_s$—R39 in which t is 1-6, R38 is hydrogen or (1-6C) alkyl, s is 0, 1 or 2, and R39 is (1-6C)alkyl or (1-6C)alkoxy, or R31 is (3-8C)alkanoylmethyl, benzoylmethyl, (1-6C)primaryhydroxyalkyl, (1-6C)primaryaminoalkyl, (1-4C)alkylamino(1-6C)alkyl, di(1-4C)alkylamino(1-6C)alkyl, (1-4C)alkoxy(1-4C)alkyl, (1-6C)alkoxy, (1-4C)alkoxy(2-4C)alkoxy(1-4C)alkyl, (1-6C)alkylamino, phenyl(1-6C)alkyl or phenyl(1-6C)alkoxy or of the formula $(CH_2)_2$N=CR40NR41R42 or $(CH_2)_2$C(NR40)NR41R42 or a tautomer thereof in which R40, R41 and R42 are hydrogen or (1-4C)alkyl, or R31 is phenyl, vinyl, cyanomethyl, 2-ureidoethyl, 2-thiouredioethyl, 2-(thioacetylamino)ethyl, sulphamoyl, 2-amino-2-carboxyethyl, acetylaminomethyl, 4,5-dihydroimidazol-2-ylmethyl, 3,4,5,6-tetrahydropyrimidin-2-ylmethyl, 2-hydroxyiminopropyl (syn or anti) or 2-[(1-4C)alkoxyimino]propyl (syn or anti), or —R31 is of the formula $(CH_2)_2$—⊕NR43R44R45 in which R43, R44 and R45 are (1-4C)alkyl, or —R31 is of the formula $(CH_2)_s$—R46 in which s is 0-2 and R46 is pyridine, pyridazine, pyrimidine, pyrazine, 1,2,5,6-dihydro-5,6-dioxo-1,2,4-triazine, 2-[(1-4C)alkyl]1,2,5,6-dihydro-5,6-dioxo-1,2,4-triazine, 1-[(1-4C)alkyl]tetrazole, furan, thiophene, pyrrole, 1-[(1-4C)alkyl]pyrrole, oxazole, thiazole, imidazole 1-[(1-4C)alkyl]imidazole, isoxazole, isothiazole, pyrazole, 1-[(1-4C)alkyl]pyrazole, benzfuran, benzthiophene, indole, 1-[(1-4C)alkyl]indole, benzoxazole, benzthiazole, benzimidazole, 1-[(1-4C)alkyl]benzimidazole, each of these ring systems being linked to $(CH_2)_s$ through carbon and each ring system being optionally substituted by halogen, (1-6C)alkyl, carboxy, (2-6C)alkoxycarbonyl, (1-6C)alkoxy, cyano, carbamoyl, hydroxy, nitro or amino;

or R30 and R31 are joined to form, together with the nitrogen to which they are attached, a 5- to 7-membered saturated ring, optionally containing an oxygen and optionally substituted by (1-4C)alkyl, n, R26, R27, R28 and R29 having the meanings given above;

or when n=1 R27 and R30 are joined to form, together with the C—C—C—N chain to which they are attached, a doubly-unsaturated 5- to 7-membered ring which is optionally substituted by (1-4C)alkyl, phenyl or benzyl and R28 and R29 are hydrogen or are joined to form, together with the C—C chain to which they are attached, a 5- to 7-membered carbocyclic ring, itself optionally substituted by (1-4C)alkyl, phenyl or benzyl, R26 and R31 having the meanings given above;

or when n=1 R27 and R28 are joined to form, together with the C—C chain to which they are attached, a singly-unsaturated 4- to 7-membered carbocyclic ring which is optionally substituted by (1-4C)alkyl, phenyl or benzyl, R26, R29, R30 and R31 having the meanings given above;

or when n=1 R26 and R30 are joined as an ethylene chain to form, together with the N—C—C—C—N chain to which they are attached, a doubly-unsaturated 7-membered ring to which is optionally fused, in the said ethylene chain, a benzene ring, said mono- or bicyclic ring system being optionally substituted by (1-4C)alkyl, phenyl or benzyl, and R27, R28 and R29 are hydrogen, R31 having the meaning given above;

or when n=1 R28 and R29 are joined to form, together with the C—C chain to which they are attached, a 4- to 7-membered ring which may optionally be substituted by (1-4C)alkyl, phenyl or benzyl, R26, R27, R30 and R31 having the meanings given above;

or when n=1 R27 and R29 are joined to form, together with the C—C—C chain to which they are attached, a singly unsaturated 5- to 7- membered ring which may optionally be substituted by (1-4C)alkyl, phenyl or benzyl, R26, R28, R30 and R31 having the meanings given above;

R32, R33, R34 and R35 are selected from hydrogen, (1-4C)alkyl, phenyl or benzyl, or R32 and R33 and/or R34 and R35 are joined to form, together with the nitrogen to which they are attached, a 5- to 7-membered saturated ring optionally containing an oxygen and optionally substituted by (1-4C)alkyl, or R33 and R34 are joined as an ethylene bridge to form, together with the N—C—C—C—N chain to which they are attached, a 7-membered ring and R36 and R37 are selected from hydrogen, amino, hydroxy, mercapto, (1-4C)alkyl, (1-6C)alkoxy, (1-6C)alkythio, (1-6C)alkylamino, (2-8C)dialkylamino, phenyl and benzyl, R26 having the meaning given above;

b is 2 or 3 and the ring in formula VII is optionally substituted by (1-4C)alkyl, phenyl or benzyl;

provided that when a phenyl or benzyl radical is present in formula IV,V,VI,VII or VIII the benzene ring therein is optionally substituted by 1 or 2 substituents selected from halogen, (1-4C)alkyl, (1-4C)alkoxy, trifluoromethyl, carboxy, hydroxy, carbamoyl, sulpho, amino, nitro and cyano;

and the salts formed with acids and bases which afford pharmaceutically-acceptable anions and cations respectively.

It is to be understood that in the above formula I and throughout this specification the illustrated stereochemistry of the ceph-3-em nucleus, and its optional modification at the 1-position, is the absolute stereochemistry. It is also to be understood that although the double bonds in formulae IV to VII inclusive have been inserted in particular positions, other tautomeric forms are, in certain instances, possible, and this invention includes such tautomeric forms within its scope. It is further to be understood that although the substituents on the each double bond in formulae IV to VII inclusive represents a specific geometric isomer, the alternative geometric isomer is in each case within the scope of this invention.

A particular value for R2 is hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methycyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, triphenylmethyl, 2-chloroethyl, 2-bromoethyl, 2-hydroxyethyl, 3-hydroxypropyl, 2-methoxyethyl, 2-ethoxyethyl, 2-methylthioethyl, 2-methanesulphinylethyl, 2-methanesulphonylethyl, 2-aminoethyl, 3-aminopropyl, 2-methylaminoethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)ethyl, tetrahydropyran-2-yl, thietan-3-yl or 2-oxo-tetrahydrofuran-3-yl, or of the formula —(Ch$_2$)$_v$—R6 in which v is 1 to 4 and R6 is piperidino, pyrolidino, morpholino, piperazino or N-methylpiperazino, each value of R6 being optionally substituted by methyl, phenyl or benzyl, or of the formula —(Ch$_2$)$_m$—W—R7 in which m is 0 to 3, W is sulphur or a direct bond and R7 is phenyl, pyridiniomethylene, 2-pyridinioethylene, pyridyl, imidazolyl, 1,3,4-thiadiazolyl, tetrazolyl, 1-methyltetrazolyl, thiazolyl, isothiazolyl or isoxazolyl in which the link with W is via a carbon or uncharged nitrogen, each value of R7 being optionally substituted, where possible, by one or two groups selected from methyl, amino, hydroxy, carboxy, carbamoyl, nitro, methoxycarbonyl, ethoxycarbonyl, cyano and sulpho, or of the formula —(Ch$_2$)$_v$—CO—R8 in which v is 1 to 4 and R8 is methyl, ethyl, phenyl or benzyl, or of the formula —COR9 or —(Ch$_2$)$_v$—OCO—R9 in which v is 1-4 and R9 is hydrogen, methyl, chloromethyl, bromomethyl, 2-chloroethyl, 2-bromoethyl, phenyl or benzyl, or of the formula —G—CH$_2$—R10 in which G is carbonyl or a direct bond and R10 is phthalimido, or of the formula —⊕NR11R12R13 in which R11, R12 and R13 are methyl or ethyl, or R11 is methyl or ethyl and R12 and R13 are joined to form a cyclopropyl, cyclobutyl, cyclopentyl or cyclohexyl ring, or R11, R12, and R13 are joined to form a 1-azonia-4-azobicyclo[2,2,2]octane or 1-azonia-3,5,7-triazatricyclo[3,3,1,1$^{3,7}$]decane, or of the formula II in which p is 1 or 2 and R14 and R15 are hydrogen or methyl, or of the formula —P(O)R16R17 in which R16 is hydroxy, methoxy, ethoxy, dimethylamino, diethylamino, phenoxy, phenylamino, or one of the particular values given above for R6, and R17 is methyl, ethyl, methoxy, ethoxy, dimethylamino, diethylamino, phenoxy, phenylamino, piperidino, pyrrolidino, morpholino, piperazino or N-methylpiperazino, or of the formula —CH$_2$P(O)R18R19 in which R18 and R19 are hydroxy, methoxy or ethoxy, or of the formula —CH(SR20)COOR21 in which R20 is methyl or ethyl and R21 is hydrogen, methyl, ethyl or isopropyl, or of the formula III in which m is 0-3, R22 is hydrogen, methyl or methylthio, R23 is hydrogen, methyl, cyclopropyl, cyclobutyl, cyclopentyl, cyclohexyl, cyano, carboxy, carboxymethyl, 2-carboxyethyl or methanesulphonylamino, or phenyl optionally substituted by amino or hydroxy, or R22 and R23 are joined to form, together with the carbon to which they are attached, a cyclopropane, cyclobutane, cyclopentane, cyclohexane or cycloheptane ring and R24 is hydroxy, amino, methoxy, ethoxy, methylamino, ethylamino, phenylamino or one of the particular values for R6 given above or of the formula NHOR25 in which R25 is hydrogen, methyl, ethyl, phenyl or benzyl, provided that when R2 contains phenyl, and unless otherwise stated above, the phenyl is optionally substituted by 1 or 2 groups selected from fluorine, chlorine, bromine, hydroxy, amino, carboxy, nitro, carbamoyl, cyano and aminomethyl.

A particular value for R3 is hydrogen or methoxy.

A particular value for R26 is hydrogen, methyl, ethyl, benzyl or $CH_2$-heteroaryl in which the heteroaryl ring is furan, thiophene, pyrrole, imidazole, oxazole, thiazole, thiadiazole, oxadiazole, triazole, pyridine, pyrimidine or pyrazine.

A particular value for R27 or R28 is hydrogen, fluorine, chlorine, bromine, methyl, ethyl or phenyl.

A particular value for R29 is hydrogen, methyl, ethyl or phenyl.

A particular value for R30 is hydrogen, methyl, ethyl, phenyl, or benzyl.

A particular value for R31 is hydrogen, amino, methyl, ethyl, cyclopropyl, cyclobutyl, cyclopentyl, cyclohexyl, allyl, 2-methoxyethyl, 2-ethoxyethyl, —$(CH_2)_t$COOR38, —$(CH_2)_t$—$CONH_2$, —$(CH_2)_t$—NH—CO—R39 or —$(CH_2)_t$S(O)$_s$—R39 in which t is 1-6, R38 is hydrogen, methyl or ethyl, s is 0,1 or 2 and R39 is methyl, ethyl, methoxy or ethoxy, or acetylmethyl, benzoylmethyl, 2-hydroxyethyl, 2-aminoethyl, 2-methylaminoethyl, 2-dimethylaminoethyl, 2-methoxyethyl, methoxy, ethoxy, 2-(2-methoxyethoxy)ethyl, methylamino, benzyl or benzyloxy or of the formula $(CH_2)_2$ $(CH_2)_2$(NR40)NR41R42 or a tautomer thereof in which R40, R41 and R42 are hydrogen or methyl, or phenyl, vinyl, cyanomethyl, 2-ureidoethyl, 2-thioureidoethyl, 2-(thioacetylamino)ethyl, sulphamoyl, 2-amino-2-carboxyethyl, acetylaminomethyl, 4,5-dihydroimidazol-2-ylmethyl 3,4,5,6-tetrahydropyrimidin-2-ylmethyl, 2-hydroxyiminopropyl (syn or anti) or 2-methoxyiminopropyl (syn or anti), or of the formula $(CH_2)_2$—⊕NR43R44R45 in which R43, R44 and R45 are methyl or ethyl, or of the formula $(CH_2)_s$—R46 in which s is 0-2 and R46 is pyridine, pyridazine, pyrimidine, pyrazine, 1,2,5,6-dihydro-5,6-dioxo-1,2,4-triazine, 2-methyl-1,2,5,6-dihydro-5,6-dioxo-1-2,4-triazine, 1-methyltetrazole, furan, thiophene, pyrrole, 1-methylpyrrole, oxazole, thiazole, imidazole, 1-methylimidazole, isoxazole, isothiazole, pyrazole, 1-methylpyrazole, benzfuran, benzthiophene, indole, 1-methylindole, benzoxazole, benzthiazole, benzimidazole, 1-methylbenzimidazole, each of these ring systems being linked to $(CH_2)_s$ through carbon and each ring system being optionally substituted by fluorine, chlorine, bromine, methyl, ethyl, carboxyl, methoxycarbonyl, methoxy, ethoxy, cyano, carbamoyl, hydroxy, nitro or amino.

A particular value for the optional substituent on the ring formed when R30 and R31 are joined is methyl or ethyl.

A particular value for the optional substituent on the ring formed when R27 and R30, or R27 and R28, or R26 and R30, or R28 and R29, are joined, is methyl, ethyl, phenyl or benzyl.

A particular value for R32, R33, R34, and R35 is one selected from hydrogen, methyl, ethyl, phenyl or benzyl.

A particular value for the optional substituent on the ring formed when R30 and R31, or R32 and R33, or R34 and R35, are joined is methyl or ethyl.

A particular value for R36 and R37 is one selected from hydrogen, amino, hydroxy, mercapto, methyl, ethyl, methoxy, ethoxy, methylthio, methylamino, dimethylamino, phenyl and benzyl.

A particular value for the optional substituent on the ring in formula VII is methyl, ethyl, phenyl or benzyl.

When a phenyl or benzyl radical is present in formula IV, V, VI, or VII, a particular value for the optional substituent on the benzene ring thereof is one or two selected from fluorine, chlorine, bromine, methyl, ethyl, methoxy, ethoxy, carboxy, hydroxy, carbamoyl, sulpho, amino, nitro and cyano.

A particular acid which affords a pharmaceutically acceptable anion is, for example, hydrochloric, hydrobromic, phosphoric, sulphuric, citric or maleic acid.

A particular base which affords a pharmaceutically acceptable cation is, for example, a base containing an alkali metal (eg sodium or potassium) or an alkaline earth metal (eg calcium or magnesium), or a primary, secondary or tertiary organic amine (eg trimethylamine, morpholine, N-methylpiperdine, N-ethylpiperidine, procaine, dibenzylamine or $N,N^1$-dibenzylethylenediamine) or other amines which have been used to form salts with cephalosporins.

Of the compounds exemplified in this application those presently preferred are those of Examples 1, 3, 5, 6, 7, 8 and 10, particularly those of Examples 3 and 6.

The cephalosporin derivative of the formula I may be manufactured by methods known in themselves for the manufacture of chemically-analogous compounds. The following processes, R1, R2, R3, R4 and X having the meanings stated above, unless indicated otherwise, are therefore provided as further features of the invention.

The process of the invention is characterised by:

(a) reaction of a compound of the formula VIII with a compound of the formula R46—R47 in which R46 is a displaceable radical [eg fluorine, chlorine, bromine, (1-6C)alkoxy, (1-6C)alkythio, (1-6C)alkanesulphinyl or (1-6C)alkanesulphonyl]and —R47 is of the formula IX, X, XI or XII;

(b) reaction of a compound of the formula XIII with an acid of the formula XIV or an activated derivative thereof;

(c) deprotection, to form carboxy, of the corresponding compound which carries a protecting group in place of the acidic hydrogen atom of the carboxy;

(d) depropection, to form a primary or secondary amino, of the corresponding compound which carries a protecting group in place of the amino hydrogen;

(e) for those compounds in which X is sulphinyl, oxidation of the corresponding compound in which X is sulphur;

(f) reaction of a compound of the formula XV with a compound of the formula R2—O—NH2;

(g) for those compounds in which R2 is other than hydrogen, reaction of a compound of the formula I in which R2 is hydrogen with a compound of the formula R46—R48 in which R46 is a displaceable radical and R48 is one of the values given above for R2, other than hydrogen.

The starting material of the formula VIII may be prepared by acylation of the appropriate 7-amino-3-azidomethylcephalosporin derivative with an acid of the formula XIV, or an activated derivative thereof, followed by reduction of the 3-azidomethyl group to the 3-aminomethyl group. During this process it may be necessary to protect amino and carboxy groups. There is thus obtained the compound of the formula VIII in which R26 is hydrogen. When R26 is other than hydrogen this group is then introduced by conventional means.

The starting material of the formula XIII may be prepared by reaction of a compound of the formula XVI with a compound of the formula R46–R47 in which R46 and R47 have the meanings stated above. During this reaction it may be necessary to protect the 7-amino and/or 4-carboxy group.

The novel starting materials described in this specification are regarded as further features of the invention. A particularly valuable starting material is that of the formula XIII.

As noted above the cephalosporin derivatives of the invention have antibacterial properties. Thus they are useful antibacterial agents, many of them having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. For example, the compounds of Examples 3 and 6 have been found to have MIC (minimum inhibitory concentration by agar-dilution technique with an inoculum size of $10^4$CFU./spot) values of less than 2 mg/1 aginst a representative strain of *Staph. aureus* and of less than than 4 mg/1 against a representative strain of *Pseudomonas aeruginosa*.

Cephalosporin derivatives have generally been found to be relatively non-toxic to warm-blooded animals and this generalisation appears to hold true for the compounds of the present invention.

According to a further feature of the invention there is provided a pharmaceutical composition which comprises a cephalosporin derivative of the invention in association with a pharmaceutically-acceptable diluent or carrier.

The pharmaceutical composition of the invention may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the cephalosporin derivative of the formula I the pharmaceutical composition of the invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 10% w/w of the cephalosporin derivative, or one suitable for oral administration in unit dosage form, for example a tablet or capsule which contains between 100 mg. and 1 g. of the cephalosporin derivative.

The pharmaceutical composition of the invention will normally be administered to man in order to combat infections caused by bacteria, in the same general manner as that employed for cephalothin, cefoxitin, cephradine and other known clinically used cephalosporin derivatives, due allowance being made in terms of dose levels for the potency of the cephalosporin derivative of the present invention relative to the known clinically used cephalosporins. Thus each patient will receive a daily intraveneous, subcutaneous or intramuscular dose of 0.5 to 50 g., and preferably 0.5 to 10 g., of the cephalosporin derivative, the composition being administered 1 to 4 times per day. The intravenous, subcutaneous and intramuscular dose will be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

The invention is illustrated, but not limited, by the following Examples. The n.m.r. spectra are quoted in delta relative to tetramethylsilane (delta=0) as internal standard, (s=singlet, d=doublet, t=triplet, q=quartet, m=multiplet, br=broad). The n.m.r. are measured at a field strength of 90 or 400 MHz. The n.m.r. solvents are as follows:

Solvent A:- d6DMSO+CD3COOD

Solvent B:- d6DMSO+CD3COOD+TFA

Solvent C:- CDCl3 +CD3COOD

The temperatures are in degrees Centigrade. The following contractions are used:

| | |
|---|---|
| TFA = | trifluoroacetic acid |
| THF = | tetrahydrofuran |
| HOAc = | acetic acid |
| EtOAc = | ethyl acetate |
| MeOH = | methanol |
| DMF = | dimethylformamide |
| DMSO = | dimethylsulphoxide |
| ether = | diethyl ether |
| HPLC = | high pressure liquid chromatography |

EXAMPLES 1–11

As a general process a solution of 3-aminomethyl-7-[2-(2-aminothiazol-4-yl)-2-((Z)-1-carboxy-1-methylethoxyamino)acetamido]ceph-3-em-4-carboxylic acid (1 equivalent) or 3-aminomethyl-7-[2-(2-aminothiazol-4-yl)-2-((Z)-methoxyimino-acetamido]ceph-3-em-4-carboxylic acid (1 equivalent) in a solvent (for example DMF or water/DMF) in the presence of 4 equivalents of base (for example triethylamine or sodium bicarbonate) was treated with an iminoether (1 equivalent) for 30 minutes in the temperature range 0° to ambient. The reaction mixture was worked up by addition of acid (eg TFA) followed by evaporation to dryness and purification of the residue by HPLC on an octadicylsiline OD3 column using a MEOH/water/HOAc mixture as eluant. The following compounds were thus prepared.

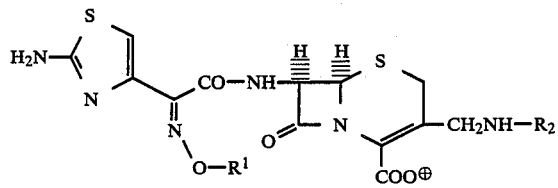

| Example | $-R^1$ | $-R^2$ | Yield % | Footnotes |
|---|---|---|---|---|
| 1 | $-C(CH_3)_2COOH$ | $-CH=\langle\text{cyclopentylidene}\rangle=\overset{\oplus}{N}(CH_3)_2$ | 40 | 1,2,3 |
| 2 | $-CH_3$ | $-CH=CH-CH=\overset{\oplus}{N}(CH_3)_2$ | 20 | 4,5,6 |
| 3 | $-C(CH_3)_2COOH$ | N-methyl dihydropyridinium | 41 | 7,5,8 |
| 4 | $-C(CH_3)_2COOCH_3$ | N-methyl dihydropyridinium | 9 | 9 |
| 5 | $-C(CH_3)_2COOH$ | cyclohexenyl=$\overset{\oplus}{N}(CH_3)_2$ | 41 | 10,2,3 |
| 6 | $-C(CH_3)_2COOH$ | cyclopentenyl-CH=$\overset{\oplus}{N}(CH_3)_2$ | 11 | 11,5,3 |
| 7 | $-C(CH_3)_2COOH$ | N-allyl dihydropyridinium | 50 | 12,2,13 |
| 8 | $-C(CH_3)_2COOH$ | dihydropyridinium $N^{\oplus}-H$ | 20 | 14,2,15 |
| 9 | $-C(CH_3)_2COOCH_3$ | dihydropyridinium $N^{\oplus}-H$ | 7 | 16 |
| 10 | $-C(CH_3)_2COOH$ | bicyclic $N^{\oplus}-CH_3$ | 24 | 17,2,3, |

-continued

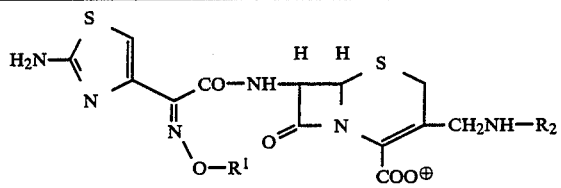

| Example | —R¹ | —R² | Yield % | Footnotes |
|---------|-----|-----|---------|-----------|
| 11 | —C(CH₃)₂COOH | ⟋⟍⟋N(CH₃)₂ with Cl | 32 | 18,19,8 |

Example 1: nmr in solvent B:—1.6(s,6H); 2.84(t,2H); 3.36(s,6H); 3.64(s,2H); 4.36(s,2H); 5.22(d,1H); 5.92 (d,1H); 7.08(s,1H); 8.12(s,1H).

Example 2: nmr in solvent A:—3.04, 3.1 (s,s. 3H); 3.3(s,3H); 3.5(m,2H);3.98(s,3H); 4.34(m,2H); 5.2 (d,1H); 5.6(m,1H); 5.84(d,1H);6.98(s,1H);7.8(m,2H).

Example 3: nmr in solvent B:—1.6(m,6H); 2.84(t,2H); 3.3(s,3H); 3.64(t,2H); 4.4(m,2H); 5.24(d,1H); 5.3 (m,1H); 5.94(d,1H); 7.12(s,1H); 7.88(m,1H).

Example 4: nmr in solvent B:—1.6(m,6H); 2.8(t,2H); 3.28(s,3H); 3.6(t,2H); 3.68(s,3H); 4.36(m,2H); 5.2 (d,1H); 5.3(m,1H); 5.9(d,1H); 7.06(s,1H); 7.84(m,1H).

Example 5: nmr in solvent B: —1.58(s,6H); 3.18(s,3H); 3.26(s,3H); 3.76(m,2H); 4.42(m,2H);5.24(d,1H); 5.52 (s,1H); 5.9(d,1H); 7.1(s,1H).

Example 6: nmr in solvent A:—1.5(s,6H); 2.5(t,2H); 2.8(t,2H); 3.56(m,2H); 4.42(m,2H); 5.2(d,1H); 5.9(d,1H); 6.8(s,1H); 8.06(s,1H).

Example 7: nmr in solvent B:—1.6(s,6H); 2.8(t,2H); 3.6(m,4H); 4.16(d,2H); 4.36(m,2H); 5.3(m,4H); 5.9 (m,2H); 7.06(s,1H); 7.9(d,1H).

Example 8: nmr in solvent B:—1.56 (s,6H); 2.76(t,2H); 3.6(m,4H); 4.4(s,2H); 5.2(d,1H); 5.34(d,1H); 5.9 (d,1H); 7.02(s,1H); 7.9(m,1H).

Example 9: nmr in solvent B:—1.58 (s,6H); 2.76(t,2H);3.6(m,4H); 4.38(s,2H); 5.2(m,2H); 5.9(d,1H); 7.06(s,1H); 7.9(m,1H).

Example 10: nmr in solvent B: —1.55(s,6H); 2.5–3.0 (m,6H); 3.2(s,3H); 3.4–3.8(m,4H); 4.3(d,1H); 4.5(d,1H); 5.2(d,1H); 5.9(d,1H); 7.05(s,1H);

Example 11: nmr in solvent B:—1.55(s,6H); 3.32(s,3H); 3.5(s,3H); 3.6(m,2H); 4.4(m,2H);5.2(d,1H); 5.9(d,1H); 7.05(s,1H); 8.05(m,2H).

Footnotes

1. The starting material, [2-(methoxymethylene)-cyclopentylidene]dimethylammonium methyl sulphate, was obtained by reaction of 1-dimethylamino-2-formylcyclopentane with one equivalent of dimethyl sulphate in a small amount of methylene chloride over 18 hours. nmr in CDCl₃:—2.0(m2H); 2.7(t,2H); 2.96(t,2H); 3.5, 3.6, 3.8, 4.2 (s,s,s,3H); 8.08(s,1H).

2. Reaction carried out in anhydrous DMF in presence of 4 equivalents of triethylamine at 0°.

3. HPLC eluant MeOH/water/HOAc 30:69:1 v/v/v.

4. The starting material was (3-methoxyprop-2-enylidene)dimethylammonium methyl sulphate.

5. Reaction carried out in DMF/water 5:2 v/v at 0° ambient temperature in presence of 4 equivalents of sodium bicarbonate for 30 minutes.

6. HPLC eluant MeOH/water/HOAc 13:86:1 v/v/v.

7. The starting material, 2,3-dihydro-4-methoxypyridinium methyl sulphate, was prepared by reaction of 1,2,3,4-tetrahydro-1-methyl-4-oxopyridine with one equivalent of dimethyl suophate at ambient temperature for 14 hours. nmr in CDCl₃:—2.9(t,2H); 3.7(s,3H); 4.0(s,6H); 5.74(d,1H); 8.56(d,1H).

8. HPLC eluant MeOH/water/HOAc 25:74:1 v/v/v.

9. This compound was obtained as a by-product in the preparation of Example 3.

10. The starting material, [3-methoxycyclohex-2-enylidene]dimethylammonium methyl sulphate, was prepared by reaction of 3-dimethylaminocylohex-2-enone with one equivalent of dimethyl sulphate at ambient temperature for 24 hours. nmr in CDCl₃:—2.04(t,2H); 2.52(t,2); 2.84(t,2H); 3.52(s,3H); 3.54(s,3H); 3.62(s,3H);3.94 (s,3H);5.92(m,1H).

11. The starting material was (2-methylcyclopent-1-enylmethylene)dimethylammonium methyl sulphate.

12. The starting material was obtained as follows. Reaction of 1,2,3,4-tetrahydro-4-oxopyridine with 2 equivalents of allyl bromide and potassium carbonate in acetone under reflux for 15 hours gave, after purficiation by silica gel/EtOAc chromatography, 1,2,3,4,-tetrahydro-1-allyl-4-oxopyridine, nmr in CHCl₃:—2.5 tetrahydro-1-allyl4-oxopyridine, nmr in CHCl₃:—2.5 (t,2H); 3.46(t,2H); 3.8(d,2H); 5.0(d,1H); 5.24(m,1H); 5.4(m,1H); 5.4(m,1H); 5.8(m,1H); 7.06(d,1H). Reaction of this compound with dimethylsulphate at ambient temperature for 18 hours gave 1-allyl-2,3-dihydro-4-methoxypyridineium methyl sulphate. nmr in CDCl₃:—2.86(t,2H); 3.68(s,3H); 3.94(t,2H0; 3.96(s,3H); 4.5 (d,2H); 5.4(d,1H); 5.56(d,2H); 5.8(d,1H); 5.9(m,1H); 8.62(d,1H0.

13. HPLC eluant MeOH/water/HOAc 27:72:1 v/v/v.

14. The starting material was 2.3-dihydro-4-methoxypyridinium methyl sulphate.

15. HPLC elunat MeOH/water/HOAc 20:79:1 v/v/v.

16. This compound was obtained as a by product in Example 8.

17. The starting material, 2,3,6,7-tetrahydro-4-methoxy-1-methylcyclopena[b]pyridinium methyl sulphate, was obtained by reaction of 2,3,4,5,6,7-hexahydro1-methyl-4-oxo-1H-cyclopenta[b]pyridine with one equivalent of dimethyl sulphate at ambient temperature for 18 hours. nmr in CDCl₃:—1.9–2.2(m,2H); 2.5–3.0 (m,6H); 3.5(s,3H); 3.7(s,3H); 4.05(s,3H); 3.9–4.1(m,2H).

18. The starting material was (2-chloro-3-dimethylaminoprop-2-enylidene)dimethylammonium perchlorate.

19. Reaction carried out in DMF/water 5:2 v/v in presence of 2 equivalents of sodium bicarbonate at ambient temperature for 30 minutes.

The 3-aminomethylcephalosporin derivatives used as starting materials may be prepared as follows.

Preparation 1

To a stirred mixture of DMF (5.8 ml.) in anhydrous methylene chloride (415 ml.) at −10° was added dropwise oxalyl chloride (6.15 ml.). Stirring was continued at −10° for 30 minutes to give a gelatinous white precipitate of (chloromethylene)dimethylammonium chloride. To this stirred suspension was added powdered 2-((Z)-1-t-butoxycarbonyl-1-methylethoxyimino)-2-(2-tritylaminothiazol-4-yl)acetic acid (40.0 g.) followed by N-methylmorpholine (8.8 ml.). Stirring was continued for 30 minutes between −5°and −15°.

In another flask a suspension of 7-amino-3-azidomethylceph-3-em-4-carboxylic acid (17.85 g.) in anhydrous methylene chloride (150 ml.) was stirred for 1 hour with N,O-bis(trimethylsilyl)acetamide (34.5 ml.) to give a clear orange solution. This was transferred by syringe to the above acid chloride solution which was stirred at −10° during the addition. The reaction mixture was then allowed to warm to room temperature and stirred for a further 90 minutes. The mixture was then poured into water (500 ml.) and extracted with EtOAc (3 x 500 ml.). The combined EtOAc extracts were washed with water, dried (Na$_2$SO$_4$) and the solvent was evaporated under reduced pressure to yield a buff foam. The crude product was dissolved in methylene chloride and applied to a column of Kieselgel 60 (125 g.). Elution with methylene chloride/MeOH/HOAc 96:2:2 v/v/v gave 3-azidomethyl-7-[2-(2-tritylaminothiazol-4-yl)-2-((Z)-1-t-butoxycarbonyl-1-methylethoxyimino)acetamido]-ceph-3-em-4-carboxylic acid (46.4 g.) as a white foam. n.m.r. in solvent A:- : 1.3 (s,9H); 1.35 (s, 6H); 3.37 (d,1H); 3.65 (d,1H); 3.9 (d,1H); 4.35 (d,1H); 5.1 (D,1H); 5.7N (d,1H); 6.66 (s,1H); 7.25 (s,15H).

An aqueous slurry of Raney nickel (10.2 g.) was added in one portion to a stirred solution of the azide (20.0 g.) in a mixture of MeOH (60 ml.) and TFA (60 ml.) at room temperature. A vigorous effervescence was observed. Stirring was continued for 1 hour and the Raney nickel was removed by filtration through diatomaceous earth. The filter pad was washed well with MeOH and the washings were combined with the filtrate. The solvents were evaporated under reduced pressure to give a pale green solid residue which was then stirred for 2 hours with a mixture of TFA (60 ml.) and water (15ml.). This mixture was evaporated to dryness and the residue was stirred vigorously with water (400 ml.) for 30 minutes. The resulting solution was filtered through diatomaceous earth to remove the undissolved triphenylmethanol and the filtrate was applied to a column of Diaion HP 20 resin (1 l.). The column was eluted with water (500 ml.) to remove inorganic material and then was aqueous MeOH 1:1 v/v. The fractions which were shown by HPLC to contain the product were evaporated under reduced pressure to yield 3-aminomethyl-7-[2-(2-aminothiazol-4-yl)-2-((Z-1-carboxy-1-methylethoxyimino)acetamido]cep-3-em-4-carboxylic acid (4.2 g.) as a pale yellow foam having the following n.m.r. in solvent A:- 1.4 (s,6H); 3.1-3.8 (complex, 4H); 4.95 (d,1H); 5.7(d,1H); 6.72 (s,1H).

Preparation 2

To a solution of cefotaxime (5.24 g.) in phosphate buffer (pH 6.4, 440 ml.) was added sodium azide (2.86 g.) and sodium iodide (1.65 g.) and the mixture was immersed in a 70° bath with stirring for 4.5 hours. The solvent was evaporated to the point of precipitation and then the pH adjusted to 2.5 with 2N aqueous HCl. The resulting precipitate was collected, washed with water, acetone and ether and dried over P$_2$O$_5$ to give 3-azidomethyl-7-[2-(2-aminothiazol-4-yl)-2-((Z)-methoxyimino)acetamido]ceph-3-em-4-carboxylic acid in quantative yield, having the following n.m.r. in solvent A:- 3.4 (d,1H); 3.7 (d,1H); 3.86 (s,3H); 3.95 (d,1H); 4.4 (d,1H); 5.15 (d,1H); 5.78 (d,1H); 6.75 (s,1H).

To a stirred suspension of Raney nickel (16 g.) in MeOH (13 ml.) at 0° was added a solution of 3-azidomethyl-7-[2-(2-aminothiazol-4-yl)-2-((Z)-methoxyimino)acetamido]ceph-3-em-4-carboxylic acid (2.96 g.) in MeOH/TFA (14 ml., 1.13 ml.). After effervescence ceased the mixture was diluted with MeOH and filtered through paper. The filtrate was evaporated, the residue purified by HPLC using water/HOAc/MeOH 79:1:20 v/v/v as eluant and the product dried over P$_2$O$_5$to give 3-aminomethyl-7-[2-(2-aminothiazol-4-yl)-2-((Z)-methoxyimino)acetamido]ceph-3-em-4-carboxylic trifluoroacetate (yield 45%) having the following n.m.r. in solvent A:- 3.5-4.2 (m,4H); 3.9 (s,3H); 5.15 (d,1H); 5.85 (d,1H); 6.75 (s,1H). The corresponding zwitterionic form was produced by passing an aqueous solution through an ion exchange column.

FORMULAE

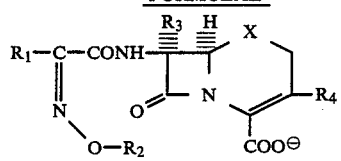

I

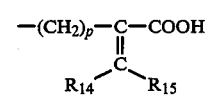

II

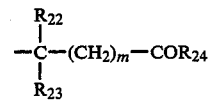

III

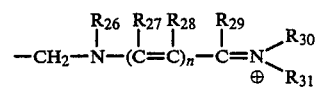

IV

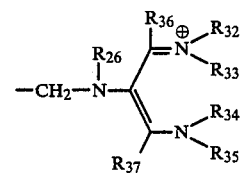

V

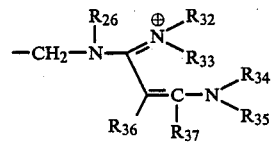

VI

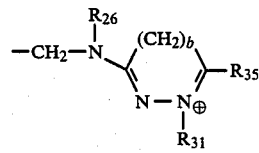

VII

-continued
FORMULAE

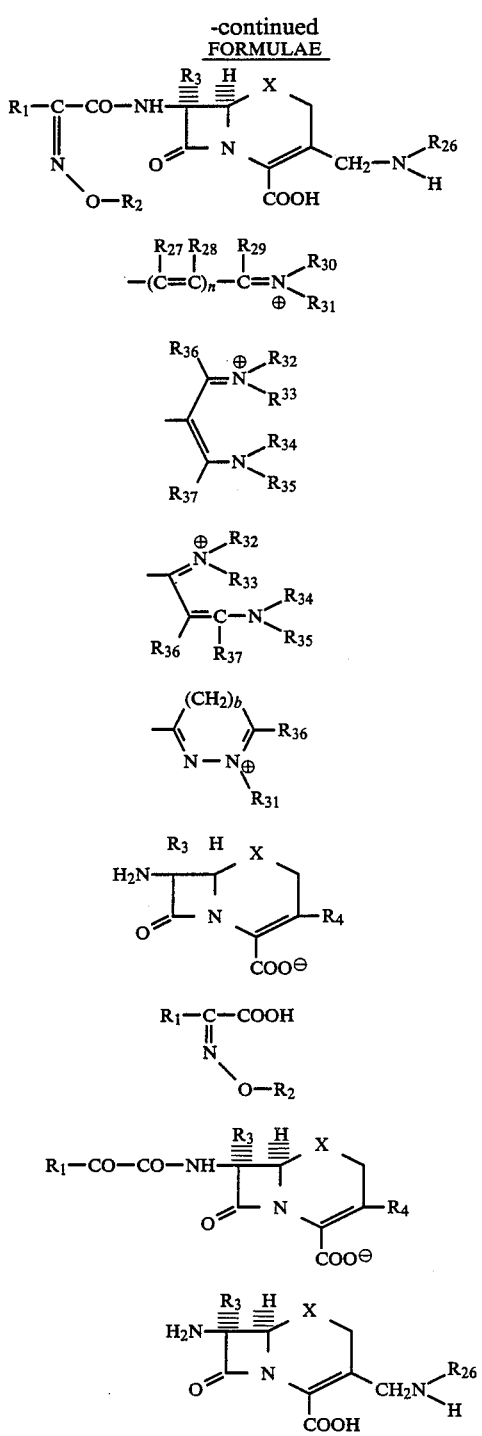

We claim:
1. A cephalosporin derivative of the formula I

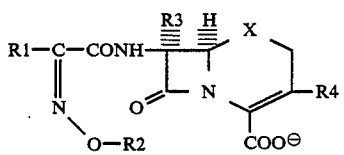

in which X is sulphur or sulphinyl (R or S configuration);

R1 is 2-aminothiazol-4-yl optionally substituted in the 5-position by fluorine, chlorine or bromine, R2 is hydrogen, (1-6C)alkyl, (3-8C)cycloalkyl, (1-3C)alkyl(3-6C)cycloalkyl, (3-6C)cycloalkyl(1-3C)alkyl, (3-6C)alkenyl, (5-8C)cycloalkenyl,(3-6C)alkynyl, (2-5C)alkylcarbamoyl, phenylcarbamoyl, benzylcarbamoyl, triphenylmethyl, (1-3C)haloalkyl, (2-6C)hydroxyalkyl, (1-4C)alkoxy(2-4C)alkyl, (1-4C)alkylthio(2-4C)alkyl, (1-4C)alkanesulphinyl(1-4C)alkyl, (1-4C)alkanesulphonyl(1-4C)alkyl, (2-6C)aminoalkyl, (1-4C)alkylamino(1-6C)alkyl, (2-8C)dialkylamino(2-6C)alkyl, (1-5C)cyanoalkyl, (1-4C)azidoalkyl, (2-5C)ureidoalkyl, 3-amino-3-carboxypropyl, 2-(amidinothio)ethyl, 2-(N-aminoamidinothio)ethyl, tetrahydropyran-2-yl, thietan-3-yl or 2-oxotetrahydro-furan-3-yl, or —R2 is the formula —(Ch$_2$)$_v$—R6 in which v is 1 to 4 and R6 is piperidino, pyrrolidino, morpholino, piperazino or N-methylpiperazino, each value of R6 being optionally substituted by (1-4C)alkyl, phenyl or benzyl, or —R2 is of the formula —(Ch$_2$)$_m$—W—R7 in which m is 0 to 3, W is sulphur or a direct bond, and R7 is phenyl or pyridinio(1-4C)alkylene or R7 is pyridyl, imidazolyl, 1,3,4-thiadiazolyl, tetrazolyl, 1-(1-4C)alkyltetrazolyl, thiazolyl, isothiazolyl or isoxazolyl in which the link with W is via a carbon or uncharged nitrogen, each value of R7 being optionally substituted, where possible, by one or two groups selected from (1-4C)alkyl, amino, hydroxy, carboxy, carbamoyl, nitro, (2-5C)alkoxycarbonyl, cyano or sulpho, or —R2 is of the formula —(Ch$_2$)$_v$—CO—R8 in which v is 1 to 4 and R8 is (1-4C)alkyl, phenyl or benzyl, or —R2 is of the formula —COR9 or —(Ch$_2$)$_v$—OCO—R9 in which v is 1-4 and R9 is hydrogen, (1-4C)alkyl, (1-4C)haloalkyl, phenyl or benzyl, or —R2 is of the formula —G—CH-$_2$—R10 in which G is carbonyl or a direct bond and R10 is phthalimido, or —R2 is of the formula II $$-(CH_2)_p-\underset{\underset{R15}{\underset{|}{C}}}{\overset{\underset{R14}{\overset{|}{}}}{C}}-COOH \qquad \text{II}$$

in which p is 1 or 2 and R14 and R15 are hydrogen or (1-4C)alkyl, or —R2 is of the formula —P(O)R16R17 in which R16 is hydroxy, (1-4C)alkoxy, (2-8c)dialkylamino, phenoxy, phenylamino or one of values given above for R6, and R17 is (1-4C)alkyl, (1-4)C)alkoxy, (2-8C)dialkylamino, phenoxy, phenylamino, piperidino, pyrrolidino, morpholino, piperazino or N-methylpiperazino, or —R2 is of the formula —CH$_2$P(O)R18R19 in which R18 and R19 are hydroxy or (1-4C)alkoxy, or —R2 is of the formula —CH(SR20)COOR21 in which R20 is (1-4C)alkyl and R21 is hydrogen or (1-6C)alkyl, or —R2 is of the formula III

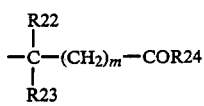

in which m is 0-3, R22 is hydrogen, (1-3C)alkyl or methylthio, R23 is hydrogen, (1-3C)alkyl, ($C_3$—$C_7$)-cycloalkyl, cyano, carboxy, (2-5C)carboxyalkyl or methanesulphonylamino, or phenyl optionally substituted by amino or hydroxy, or R22 and R23 are joined to form, together with the carbon to which they are attached, a (3-7C) carbocyclic ring and R24 is hydroxy, amino, (1-4C)alkoxy, (1-4C)alkylamino, phenylamino or of the formula R6 given above or of the formula NHOR25 in which R25 is hydrogen, (1-4C)alkyl, phenyl or benzyl, provided that when R2 contains phenyl, and unless otherwise stated, the phenyl is optionally substituted by 1 or 2 groups selected from halogen, hydroxy, amino, carboxy, nitro, carbamoyl, cyano and aminomethyl;

R3 is hydrogen or methoxy;

—R4 is of the formula IV,V,VI, or VII:

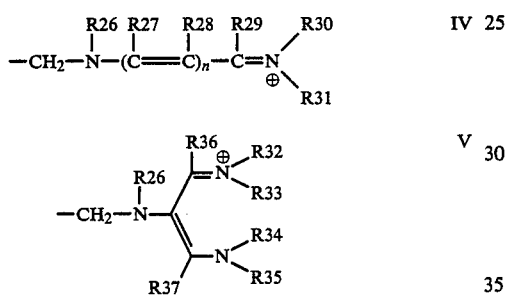

in which n is 1-3;

R26 is hydrogen, (1-4C)alkyl, benzyl or $CH_2$heteroaryl in which the heteroaryl ring is a 5- or 6-membered aromatic ring containing 1,2 or 3 hetero atoms selected from O, N and S;

R27 and R28 are selected from hydrogen, halogen, (1-4C)alkyl and phenyl;

R29 is hydrogen, (1-4C)alkyl or phenyl;

R30 is hydrogen, (1-4C)alkyl, phenyl or benzyl;

R31 is hydrogen, amino, (1-4C)alkyl, (3-6C)cycloalkyl, (3-6C)alkenyl, (2-8C)alkoxyalkyl, —($CH_2$)$_t$—COOR38, —($CH_2$)$_t$—CONH$_2$, —($CH_2$)$_t$—NHCO—R39 or —($CH_2$)$_t$S(O)$_s$—R39 in which t is 1-6, R38 is hydrogen or (1-6C)alkyl, s is 0, 1 or 2, and R39 is (1-6C)alkyl or (1-6C)alkoxy, or R31 is (3-8C)alkanoylmethyl, benzoylmethyl, (1-6C)primaryhydroxyalkyl, (1-6C)primaryaminoalkyl, (1-4C)alkylamino(1-6C)alkyl, di(1-4C)alkylamino(1-6C)alkyl, (1-4C)alkoxy(1-4C)alkyl, (1-6C)alkoxy, (1-4C)alkoxy(2-4C)alkoxy(1-4C)alkyl, (1-6C)alkylamino, phenyl(1-6C)alkyl or phenyl(1-6C)alkoxy or of the formula ($CH_2$)$_2$N=CR40NR41R42 or ($CH_2$)$_2$C(NR40)NR41R42 or a tautomer thereof in which R40, R41 and R42 are hydrogen or (1-4C)alkyl, or R31 is phenyl, vinyl, cyanomethyl, 2-ureidoethyl, 2-thioureidoethyl, 2-(thioacetylamino)ethyl, sulphamoyl, 2-amino-2-carboxyethyl, acetylaminomethyl, 4,5-dihydroimidazol-2-ylmethyl, 3,4,5,6-tetrahydropyrimidin-2-ylmethyl, 2-hydroxyiminopropyl (syn or anti) or 2-[(1-4C)alkoxyimino]propyl (syn or anti), or —R31 is of the formula ($CH_2$)$_2$—NR43R44R45 in which R43, R44 and R45 are (1-4C) alkyl, or —R31 is of the formula ($CH_2$)$_s$—R46 in which s is 0-2 and R46 is pyridine, pyridazine, pyrimidine, pyrazine, 1,2,5,6-dihydro-5,6-dioxo-1,2,4-triazine, 2-[(1-4C)alkyl]-1,2,5,6-dihydro-5,6-dioxo-1,2,4-triazine, 1-[(1-4C)alkyl]tetrazole, furan, thiophene, pyrrole, 1-[(1-4C)alkyl]pyrrole, oxazole, thiazole, imidazole, 1-[(1-4C)alkyl]imidazole, isoxazole, isothiazole, pyrazole, 1-[(1-4C)alkyl]pyrazole, benzfuran, benzthiophene, indole, 1-[(1-4C)alkyl]indole, benzoxazole, benzthiazole, benzimidazole, 1-[(1-4C)alkyl]benzimidazole, each of these ring systems being linked to ($CH_2$)$_s$ through carbon and each ring system being optionally substituted by halogen, (1-6C)alkyl, carboxy, (2-6C)alkoxycarbonyl, (1-6C)alkoxy, cyano, carbamoyl, hydroxy, nitro or amino;

or R30 and R31 are joined to form, together with the nitrogen to which they are attached, a 5- to 7-membered saturated ring, optionally containing an oxygen and optionally substituted by (1-4C)alkyl, n, R26, R27, R28 and R29 having the meanings given above;

or when n=1 R27 and R30 are joined to form, together with the C—C—C—N chain to which they are attached, a doubly-unsaturated 5- to 7-membered ring which is optionally substituted by (1-4C)alkyl, phenyl or benzyl and R28 and R29 are hydrogen or are joined to form, together with the C—C chain to which they are atatched, a 5- to 7-membered carbocyclic ring, itself optionally substituted by (1-4C)alkyl, phenyl or benzyl, R26 and R31 having the meanings given above;

or when n=1 R27 and R28 are joined to form, together with the C—C chain to which they are attached, a singly-unsaturated 4- to 7-membered carbocyclic ring which is optionally substituted by (1-4C)alkyl, phenyl or benzyl, R26, R29, R30 and R31 having the meanings given above;

or when n=1 R26 and R30 are joined as an ethylene chain to form, together with the N—C—C—C—N chain to which they are attached, a doubly-unsaturated 7-membered ring to which is optionally fused, in the said ethylene chain, a benzene ring, said mono- or bi-cyclic ring system being optionally substituted by (1-4C)alkyl, phenyl or benzyl, and R27, R28 and R29 are hydrogen, R31 having the meaning given above;

or when n=1 R28 and R29 are joined to form, together with the C—C chain to which they are attached, a 4- to 7-membered ring which may optionally be substituted by (1-4C)alkyl, phenyl or benzyl, R26, R27, R30 and R31 having the meanings given above;

or when n=1 R27 and R29 are joined to form, together with the C—C—C chain to which they are attached, a singly unsaturated 5- to 7-membered ring which may optionally be substituted by (1-4C)alkyl, phenyl or benzyl, R26, R28, R30 and R31 having the meanings given above.

R32, R33, R34 and R35 are selected from hydrogen, (1-4C)alkyl, phenyl or benzyl, or R32 and R33 and/or R34 and R35 are joined to form, together with the nitrogen to which they are attached, a 5- to 7-membered saturated ring optionally containing an oxygen and optionally substituted by (1-4C)alkyl, or R33 and R34 are joined as an ethylene bridge to form, together with the N—C—C—N chain to which they are attached, a 7-membered ring and R36 and R37 are selected from hydrogen, amino, hydroxy, mercapto, (1-4C)alkyl, (1-6C)alkoxy, (1-6C)alkythio, (1-6C)alkylamino, (2-8C)dialkylamino, phenyl and benzyl, R26 having the meaning given above;

b is 2 or 3 and the ring in formula VII is optionally substituted by (1-4C)alkyl, phenyl or benzyl;

provided that when a phenyl or benzyl radical is present in formula IV,V,VI,VII or VIII

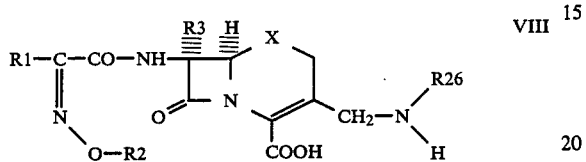

the benzene ring therein is optionally substituted by 1 or 2 substituents selected from halogen, (1-4C)alkyl, (1-4C)alkoxy, trifluoromethyl, carboxy, hydroxy, carbamoyl, sulpho, amino, nitro and cyano; and the salts formed with acids and bases which afford pharmaceutically-acceptable anions and cations respectively.

2. A compound as claimed in claim 1 in which R2 is hydrogen, methyl, ethyl, isopropyl, t-butyl, cyclopropyl, cyclobutyl, cyclopentyl, cyclohexyl, methylcyclopropyl, methylcyclobutyl, methycyclopentyl, methylcyclohexyl, cyclopropylmethyl, cyclobutylmethyl, cyclopentylmethyl, allyl, cyclopentenyl, cyclohexenyl, propargyl, methylcarbomyl, ethylcarbamoyl, phenylcarbamoyl, benzylcarbamoyl, triphenylmethyl, 2-chloroethyl, 2-bromoethyl, 2-hydroxyethyl, 3-hydroxpropyl, 2-methoxyethyl, 2-ethoxyethyl, 2-methylthioethyl, 2-methanesulphinylethyl, 2-methanesulphonylethyl, 2-aminoethyl, 3-aminopropyl, 2-methylaminoethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)ethyl, tetrahydropyran-2-yl, thietan-3-yl or 2-oxo-tetrahydrofuran-3-yl, or of the formula —(Ch2)$_v$—R6 in which v is 1 to 4 and R6 is piperidino, pyrolidino, morpholino, piperazino or N-methylpiperazino, each value of R6 being optionally substituted by methyl, phenyl or benzyl, or of the formula —(Ch2)$_m$—W—R7 in which m is 0 to 3, W is sulphur or a direct bond and R7 is phenyl, pyridiniomethylene, 2-pyridinioethylene, pyridyl, imidazolyl, 1,3,4-thiadiazolyl, tetrazolyl, 1-methyltetrazolyl, thiazolyl, isothiazolyl or isoxazolyl in which the link with W is via a carbon or uncharged nitrogen, each value of R7 being optionally substituted, where possible, by one or two groups selected from methyl, amino, hydroxy, carboxy, carbamoyl, nitro, methoxycarbonyl, ethoxycarbonyl, cyano and sulpho, or of the formula —(Ch2)$_v$—CO—R8 in which v is 1 to 4 and R8 is methyl, ethyl, phenyl or benzyl, or of the formula —COR9 or —(Ch2)$_v$—OCO—R9 in which v is 1-4 and R9 is hydrogen, methyl, chloromethyl, bromomethyl, 2-chloroethyl, 2-bromoethyl, phenyl or benzyl, or of the formula —G—CH2—R10 in which G is carbonyl or a direct bond and R10 is phthalimido, or of the formula II in which p is 1 or 2 and R14 and R15 are hydrogen or methyl, or of the formula —P(O)R16R17 in which R16 is hydroxy, methoxy, ethoxy, dimethylamino, diethylamino, phenoxy, phenylamino, or one of the particular values given above for R6, and R17 is methyl, ethyl, methoxy, ethoxy, dimethylamino, diethylamino, phenoxy, phenylamino, piperidino, pyrrolidino, morpholino, piperazino or N-methylpiperazino, or of the formula —CH2P(O)R18R19 in which R18 and R19 are hydroxy, methoxy or ethoxy, or of the formula —CH(SR20)COOR21 in which R20 is methyl or ethyl and R21 is hydrogen, methyl, ethyl or isopropyl, or of the formula III in which m is 0-3, R22 is hydrogen, methyl or methylthio, R23 is hydrogen, methyl, cyclopropyl, cyclobutyl, cyclopentyl, cyclohexyl, cyano, carboxy, carboxymethyl, 2-carboxyethyl or methanesulphonylamino, or phenyl optionally substituted by amino or hydroxy, or R22 and R23 are joined to form, together with the carbon to which they are attached, a cyclopropane, cyclobutane, cyclopentane, cyclohexane or cycloheptane ring and R24 is hydroxy, amino, methoxy, ethoxy, methylamino, ethylamino, phenylamino or one of the particular values for R6 given above or of the formula NHOR25 in which R25 is hydrogen, methyl, ethyl, phenyl or benzyl, provided that when R2 contains phenyl, and unless otherwise stated above, the phenyl is optionally substituted by 1 or 2 groups selected from fluorine, chlorine, bromine, hydroxy, amino, carboxy, nitro, carbamoyl, cyano and aminomethyl.

3. A compound as claimed in claim 1 in which R2 is methyl, ethyl, i-propyl, allyl, propargyl, cyclopentyl, cyclopropylmethyl, 2-chloroethyl, 2-bromoethyl, cyanomethyl, 2-cyanoethyl, 2-hydroxyethyl, 2-ethoxyethyl, benzyl or of the formula III in which m is 0, R22 and R23 are both hydrogen or methyl or are joined to form, together with the carbon to which they are attached, a cyclobutyl or cyclopentyl ring and R24 is hydroxy or methoxy.

4. A compound as claimed in claim 3 in which X is sulphur, R1 is 2-aminothiazol-4-yl and R3 is hydrogen.

5. A compound as claimed in claim 1 in which R4 is of the formula IV, V, VI or VII in which R26 is hydrogen, methyl, ethyl, benzyl or CH2-heteroaryl in which the heteroaryl ring is furan, thiophene, pyrrole, imidazole, oxazole, thiazole, thiadiazole, oxadiazole, triazole, pyridine, pyrimidone or pyrazine;

R27 and R28 are independently selected from hydrogen, fluorine, chlorine, bromine, methyl, ethyl or phenyl;

R29 is hydrogen, methyl, ethyl or phenyl;

R30 is hydrogen, methyl, ethyl, phenyl or benzyl;

R31 is hydrogen, amino, methyl, ethyl, cyclopropyl, cyclobutyl, cyclopentyl, cyclohexyl, allyl, 2-methoxyethyl, 2-ethoxyethyl, —(Ch2)$_t$—COOR38, —(Ch2)$_t$—CONH2, —(Ch2)$_t$—NHCO—R39 or —(Ch2)$_t$-S(O)$_s$—R39 in which t is 1-6, R38 is hydrogen, methyl, or ethyl, s is 0, 1 or 2 and R39 is methyl, ethyl, methoxy or ethoxy, or acetylmethyl, benzoylmethyl, 2-hydroxyethyl, 2-aminoethyl, 2-methylaminoethyl, 2-dimethylaminoethyl, 2-methoxyethyl, methoxy, ethoxyk 2-(2-methoxyethoxy)ethyl, methylamino, benzyl or benzyloxy or of the formula $(CH_2)_2(CH_2)_2C(NR40)NR41R42$ or a tautomer thereof in which R40, R41 and R42 are hydrogen or methyl, or phenyl, vinyl, cyanomethyl, 2-ureidoethyl, 2-thioureidoethyl, 2-(thioacetylamino)ethyl, sulphamoyl, 2-amino-2-carboxyethyl, acetylaminoethyl, 4,5-dihydroimidazol-2-ylmethyl, 3,4,5,6,-tetrahydropyrimidin-2-ylmethyl, 2-hydroxyiminopropyl (syn or anti) or 2-methoxyiminopropyl (syn or anti), or of the formula $(CH_2)_2$—NR43R44R45 in which R43, R44 and R45 are methyl or ethyl, or of the formula $(CH_2)_s$—R46 in which s is 0-2 and R46 is pyridine, pyridazine, pyrimidine, pyrazine, 1,2,5,6-dihydro-5,6-dioxo-1,2,4-triazine, 2-methyl-1,2,5,6-dihydro-5,6-dioxo-1,2,4-triazine, 1-methyltetrazole, furan, thiophene, pyrrole, 1-methylpyrrole, oxazole, thiazole, imidazole, 1-methylimidazole, isoxazole, isothiazole, pyrazole, 1-methylpyrazole, benzfuran, benzthiophene, indole, 1-methylindole, benzoxazole, benzthiazole, benzimidazole, 1-methylbenzimidazole, each of these ring systems being linked to $(CH_2)_s$ through carbon and each ring system being optionally substituted by fluorine, chlorine, bromine, methyl, ethyl, carboxy, methoxycarbonyl, methoxy, ethoxy, cyano, carbamoyl, hydroxy, nitro or amino;

or R30 and R31 are joined to form a ring as defined in claim 1 and said ring is unsubstituted or substituted by methyl or ethyl;

or n=1 and R27 and R28; or R26 and R30; or R27 and R29; or R27 and R30 and/or R28 and R29; are joined to form a ring as defined in claim 1 and such a ring is unsubstituted or is substituted by methyl, ethyl, phenyl or benzyl;

R32, R33, R34 and R35 are independently selected from hydrogen, methyl, ethyl, phenyl or benzyl, or R32 and R33 and/or R34 and R35 are joined to form a ring as defined in claim 1 and said ring is unsubstituted or substituted by methyl or ethyl;

R36 and R37 are independently selected from hydrogen, amino, hydroxy, mercapto, methyl, ethyl, methoxy, ethoxy, methylthio, methylamino, dimethylamino, phenyl and benzyl;

the ring in formula VII is unsubstituted or substituted by methyl, ethyl, phenyl or benzyl; and when a phenyl or benzyl radical is present in formula IV, V, VI, or VII, the benzene ring thereof is substituted or substituted by one or two substituents selected from fluorine, chlorine, bromine, methyl, ethyl, methoxy, ethoxy, carboxy, hydroxy, carbamoyl, sulpho, amino, nitro and cyano.

6. Compounds as claimed in claim 1 wherein X is sulphur; R3 is hydrogen; R1 is 2-aminothiazol-4-yl; R2 is methyl or of the formula III wherein R22 and R23 are methyl or are joined to form a cyclobutyl ring, m=0 and R24 is hydroxy or methoxy; and R4 is of the formula IV in which:

R26 is hydrogen, methyl or ethyl;
R31 is hydrogen, methyl, ethyl or allyl;
R27 and R28 are independently selected from hydrogen and chlorine, R29 is hydrogen and R30 is methyl or ethyl;

or R28 and R29; or R27 and R29; or R27 and R30 and/or R27 and R28 are joined to form 5- or 6-membered rings as defined in claim 1.

7. Compounds as claimed in claim 1 wherein X is sulphur; R3 is hydrogen; R1 is 2-aminothiazol-4-yl and R2 and R4 have the meanings set out in the following table:

| R2 | R4 |
| --- | --- |
| —C(CH$_3$)$_2$COOH | —CH=(cyclopentylidene)-CH=N$^{\oplus}$(CH$_3$)$_2$ |
| —CH$_3$ | CH=CH—CH=N$^{\oplus}$(CH$_3$)$_2$ |
| —C(CH$_3$)$_2$COOH | (methyl-substituted pyridinium: N$^{\oplus}$—CH$_3$) |
| —C(CH$_3$)$_2$COOCH$_3$ | (methyl-substituted pyridinium: N$^{\oplus}$—CH$_3$) |
| —C(CH$_3$)$_2$COOH | (methylcyclohexylidene)=N(CH$_3$)$_2$$^{\oplus}$ |
| —C(CH$_3$)$_2$COOH | (methylcyclopentenyl)-CH=N$^{\oplus}$(CH$_3$)$_2$ |
| —C(CH$_3$)$_2$COOH | (methylpyridinium with N$^{\oplus}$-allyl) |
| —C(CH$_3$)$_2$COOH | (methylpyridinium: N$^{\oplus}$—H) |
| —C(CH$_3$)$_2$COOCH$_3$ | (methylpyridinium: N$^{\oplus}$—H) |
| —C(CH$_3$)$_2$COOH | (bicyclic methylpyridinium: N$^{\oplus}$—CH$_3$) |
| —C(CH$_3$)$_2$COOH | CH=C(Cl)—CH=CH—N$^{\oplus}$(CH$_3$)$_2$ |

8. A pharmaceutical composition which comprises a cephalosporin derivative as claimed in claim 1 or a pharmaceutically acceptable salt thereof in association with a pharmaceutically acceptable diluent or carrier.

9. A method of treating a bacterial infection in a human or animal host which comprises administering to said host an antibacterially effective amount of a cephalosporin derivative as claimed in claim 1.

* * * * *